United States Patent
Miki et al.

(10) Patent No.: US 10,444,198 B2
(45) Date of Patent: Oct. 15, 2019

(54) PIPING INSPECTION APPARATUS

(71) Applicant: Hitachi, Ltd., Tokyo (JP)

(72) Inventors: Masahiro Miki, Tokyo (JP); Yuki Oshima, Tokyo (JP); Naoyuki Kono, Tokyo (JP); Toshimi Kimura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 217 days.

(21) Appl. No.: 15/484,324

(22) Filed: Apr. 11, 2017

(65) Prior Publication Data

US 2017/0328869 A1    Nov. 16, 2017

(30) Foreign Application Priority Data

May 12, 2016   (JP) .................. 2016-095912

(51) Int. Cl.
    *G01N 29/22*    (2006.01)
    *G01N 29/04*    (2006.01)

(52) U.S. Cl.
    CPC .......... *G01N 29/223* (2013.01); *G01N 29/04* (2013.01); *G01N 29/221* (2013.01); *G01N 2291/2634* (2013.01)

(58) Field of Classification Search
    CPC .... G01N 29/223; G01N 29/221; G01N 29/04; G01N 2291/2634
    USPC ......................................................... 73/628
    See application file for complete search history.

(56) References Cited

U.S. PATENT DOCUMENTS

| | | | |
|---|---|---|---|
| 3,299,696 A * | 1/1967 | Dickinson, III | B06B 3/00 310/326 |
| 5,251,487 A * | 10/1993 | Marshall | G01H 5/00 73/644 |
| 6,138,514 A | 10/2000 | Iwamoto et al. | |
| 7,474,092 B1 * | 1/2009 | Kwun | G01N 29/043 324/238 |
| 7,799,139 B2 * | 9/2010 | Keating | C11D 7/263 134/1.3 |
| 9,404,903 B2 * | 8/2016 | Batzinger | G01N 33/00 |
| 2002/0134161 A1 * | 9/2002 | Chinn | G01N 29/07 73/622 |
| 2011/0072905 A1 * | 3/2011 | Lam | G01N 29/221 73/622 |
| 2014/0102201 A1 | 4/2014 | Brignac et al. | |

FOREIGN PATENT DOCUMENTS

| | | |
|---|---|---|
| DE | 27 51 810 A1 | 5/1979 |
| EP | 2 031 385 A1 | 3/2009 |
| JP | 2014-081376 A | 5/2014 |

OTHER PUBLICATIONS

Extended European Search Report in corresponding European Application No. 17166434.5 dated Oct. 16, 2017.

\* cited by examiner

*Primary Examiner* — Jacques M Saint Surin (74) *Attorney, Agent, or Firm* — Mattingly & Malur, PC (57) ABSTRACT

An ultrasonic transmission probe is arranged such that an ultrasonic wave transmitted from the ultrasonic transmission probe toward a pipe propagates in a thick part of the pipe, is at least reflected on the outer peripheral face of the pipe, and travels toward an inspection site on the pipe, and an ultrasonic reception probe is arranged to be symmetrical to the ultrasonic transmission probe with reference to the xz plane including the inspection site and perpendicular to the center axis of the pipe.

10 Claims, 9 Drawing Sheets

PIPING INSPECTION APPARATUS

BACKGROUND OF THE INVENTION

1. Field of the Invention

The present invention relates to a piping inspection apparatus for inspecting the presence of damage on a pipe.

2. Description of the Related Art

Radiographic testing or ultrasonic testing is performed for damages of pipes (such as cracks on inner peripheral faces of pipes) provided in power plant or chemical plant. The radiographic testing out of the two testing methods needs the works of installing a radiation source and shielding a site to be inspected from the surrounding, and has a restriction that person's entry is limited during the inspection. It is therefore desirable that the ultrasonic testing is performed for the presence of damage on a pipe. For the ultrasonic testing, for example, JP 2014-81376 A describes that an ultrasonic wave is transmitted or received by one probe thereby to inspect the presence of damage on a pipe on the basis of a reflection wave of the ultrasonic wave.

CITATION LIST

Patent Literature

Patent Literature 1: JP 2014-81376 A

SUMMARY OF THE INVENTION

A plurality of pipes are welded in order to provide relatively longer pipes in power plant or chemical plant in many cases. In such a case, a part where pipes are welded is protruded radially outside from the outer peripheral face of the pipes ("weld reinforcement" is present). For example, with the technique described in JP 2014-81376 A, if a probe is arranged on the weld reinforcement, the probe is unstable, and the presence of damage on the pipe cannot be accurately inspected.

It is therefore an object of the present invention to provide a piping inspection apparatus for accurately inspecting the presence of damage on a pipe.

In order to achieve the object, in a piping inspection apparatus according to the present invention, an ultrasonic transmission probe is arranged such that an ultrasonic wave transmitted from the ultrasonic transmission probe toward a pipe propagates in a thick part of the pipe, is at least reflected on the outer peripheral face of the pipe, and travels toward an inspection site on the pipe, and an ultrasonic reception probe is arranged to be symmetrical to the ultrasonic transmission probe with reference to a plane including the inspection site and perpendicular to the center axis of the pipe.

Further, in a piping inspection apparatus according to the present invention, an ultrasonic transmission probe is arranged such that an ultrasonic wave transmitted from the ultrasonic transmission probe toward a pipe propagates in a thick part of the pipe, is at least reflected on the outer peripheral face of the pipe, and travels toward an inspection site of the pipe, and an ultrasonic reception probe is arranged to be symmetrical to the ultrasonic transmission probe with reference to a plane including the inspection site and the center axis of the pipe.

According to the present invention, it is possible to provide a piping inspection apparatus for accurately inspecting the presence of damage on a pipe.

DESCRIPTION OF THE PREFERRED EMBODIMENTS

First Embodiment

<Configuration of Piping Inspection Apparatus>

Figure 1:
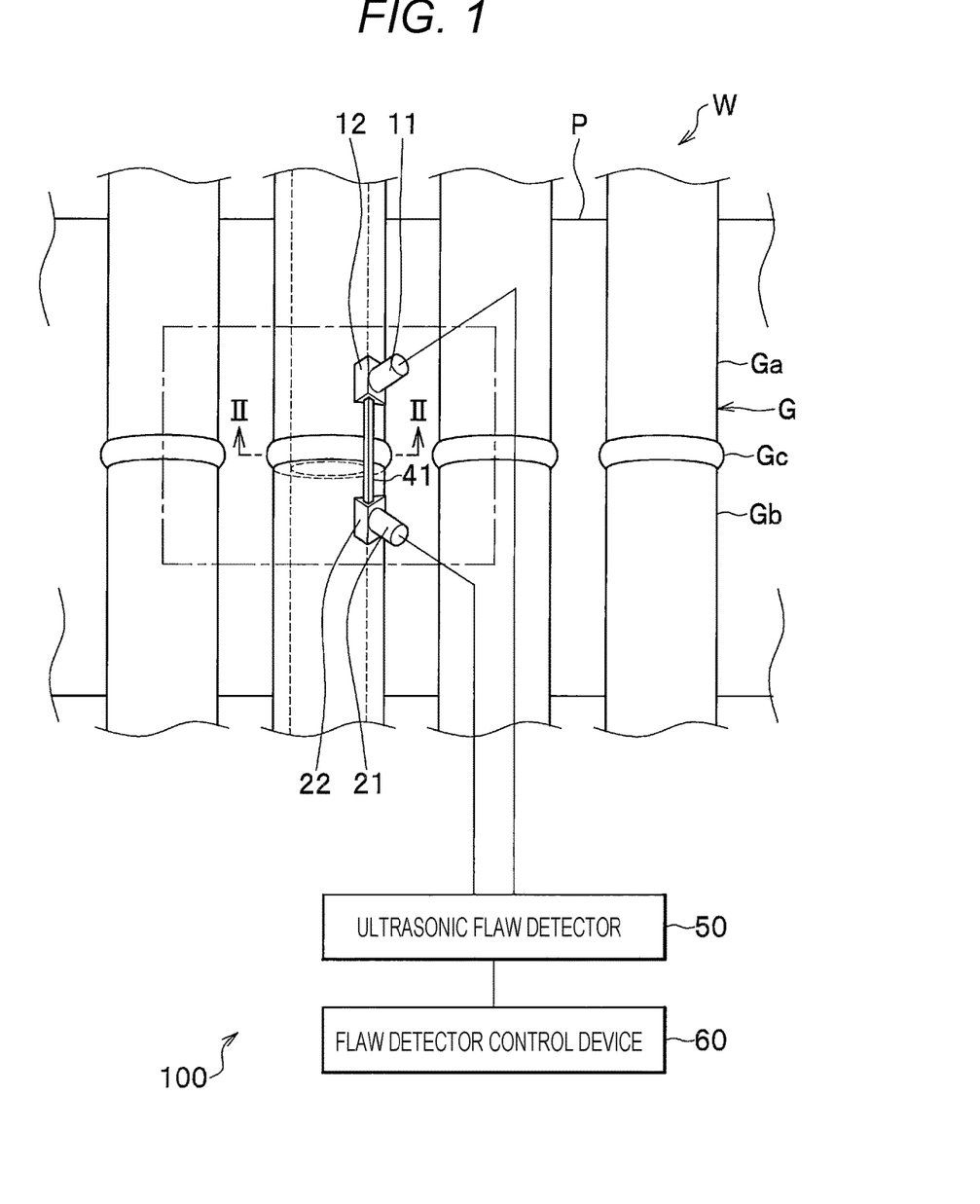
FIG. 1 is an explanatory diagram of a piping inspection apparatus according to a first embodiment of the present invention.

FIG. 1 is an explanatory diagram of a piping inspection apparatus 100 according to a first embodiment.

A water-wall W will be briefly described prior to the description of the piping inspection apparatus 100.

The water-wall W is directed for partitioning the inside and the outside of a boiler furnace (not illustrated) provided in a thermal plant (not illustrated). The water-wall W includes a plurality of pipes G through which cool water circulates, and a plurality of film plates P which are provided between the adjacent pipes G, G and are welded on the pipes G, G.

A cylindrical pipe G includes base pipes Ga, Gb, and a circumferential welded part Gc where the base pipes Ga and Gb are welded. The circumferential welded part Gc is protruded radially outside from the outer peripheral face of the base pipes Ga and Gb, where damage such as crack occurs in more cases than on the base pipes Ga and Gb. The first embodiment will be described assuming that an inspection is carried out as to whether an "axial crack" (damage) substantially parallel to the center axis of the pipe G is present on the inner peripheral face of the circumferential welded part Gc. Further, a cylindrical part where a material of the pipe G is present (or the pipe G itself) is also called "thick part Gi" (see FIG. 3).

The piping inspection apparatus 100 is directed for inspecting the presence of damage on the pipe G. As illustrated in FIG. 1, the piping inspection apparatus 100 includes an ultrasonic transmission probe 11, a wedge 12 (transmission wedge), an ultrasonic reception probe 21, a wedge 22 (reception wedge), a holding unit 41, an ultrasonic flaw detector 50, and a flaw detector control device 60 (piping inspection unit).

The ultrasonic transmission probe 11 is directed for transmitting an ultrasonic wave toward the pipe G, and is arranged on the pipe G via the wedge 12.

Figure 2:
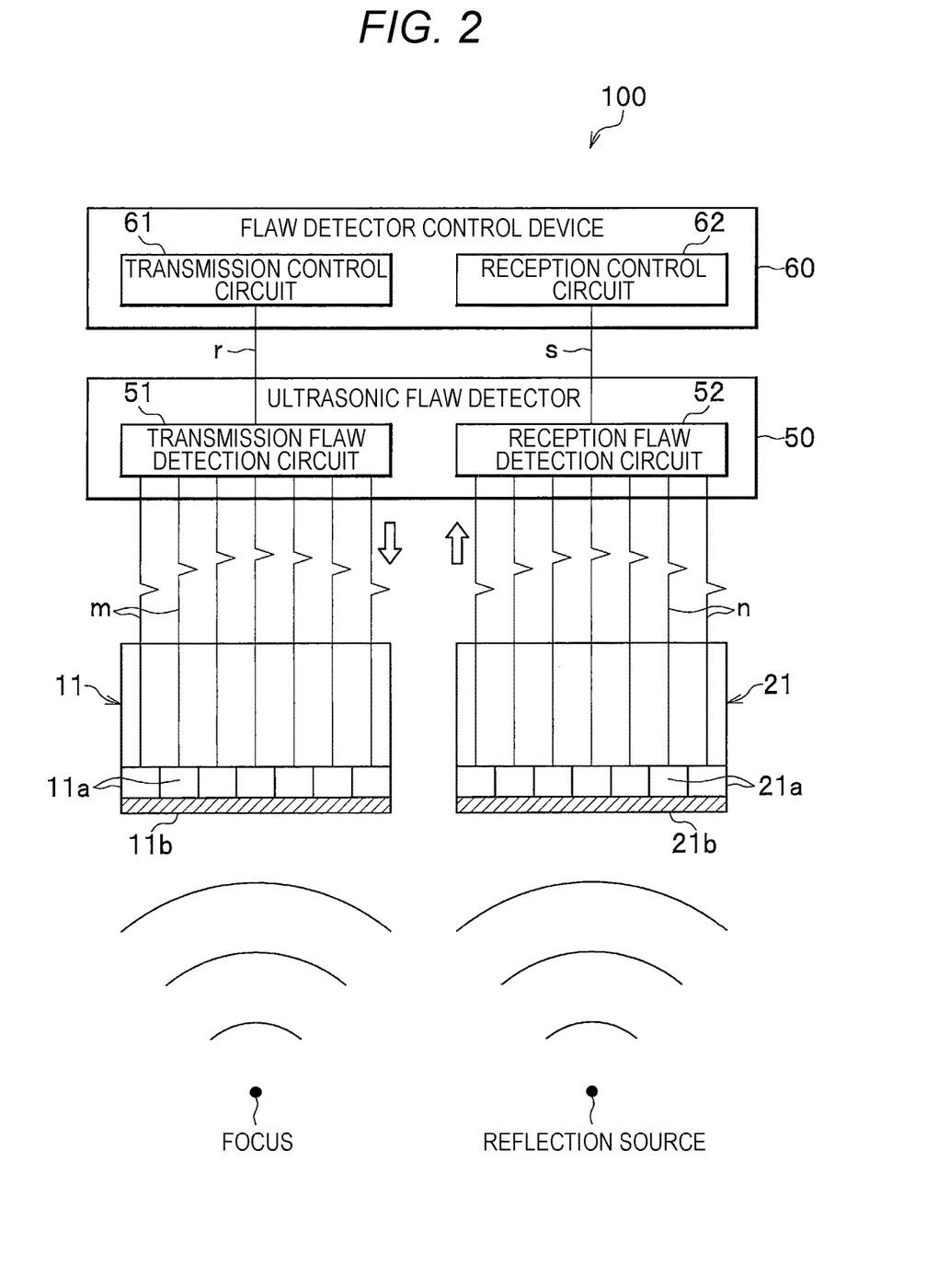
FIG. 2 is a configuration diagram of the piping inspection apparatus according to the first embodiment of the present invention.

FIG. 2 is a configuration diagram of the piping inspection apparatus 100. The wedges 12 and 22 (see FIG. 1) are not illustrated in FIG. 2.

The ultrasonic transmission probe 11 illustrated in FIG. 2 is an ultrasonic array probe including a plurality of oscillators 11a and an acoustic adjustment layer 11b. The oscillators 11a are piezoelectric devices arranged in line, and are connected to a transmission flaw detection circuit 51 via wirings m. A pulse voltage is applied from the transmission flaw detection circuit 51 to the oscillators 11a via the wirings m so that the respective oscillators 11a oscillate.

The acoustic adjustment layer 11b is a resin layer for efficiently putting an ultrasonic wave generated by oscillation of the oscillators 11a into the pipe G (see FIG. 1), and is arranged outside the oscillators 11a (closer to the pipe G).

The configuration of the ultrasonic transmission probe 11 is not limited to one illustrated in FIG. 2. For example, an acoustic lens (not illustrated) for converging an ultrasonic wave may be provided outside the acoustic adjustment layer 11b. Further, a backing member (not illustrated) for suppressing extra oscillation of the oscillators 11a may be provided inside the oscillators 11a.

The ultrasonic reception probe 21 is configured to be capable of receiving an ultrasonic wave transmitted from the ultrasonic transmission probe 11, and is arranged on the pipe G via the wedge 22 (see FIG. 1). The ultrasonic reception probe 21 is an ultrasonic array probe including a plurality of oscillators 21a and an acoustic adjustment layer 21b. The configuration of the ultrasonic reception probe 21 is similar to that of the ultrasonic transmission probe 11, and thus the description thereof will be omitted.

As illustrated in FIG. 2, an ultrasonic wave (oscillation) from a reflection source is converted into an electric signal (reflection signal) in each oscillator 21a, and the electric signal is output to a reception flaw detection circuit 52 via wirings n. The reflection source is an axial crack on the inner peripheral face of the pipe G (see FIG. 1), for example.

The ultrasonic flaw detector 50 includes, though not illustrated, electric circuits such as CPU (Central Processing Unit), ROM (Read Only Memory), RAM (Random Access Memory), and various interfaces. The ultrasonic flaw detector 50 reads the programs stored in the ROM and develops them into the RAM so that the CPU performs various processing. As illustrated in FIG. 2, the ultrasonic flaw detector 50 includes the transmission flaw detection circuit 51 and the reception flaw detection circuit 52.

The transmission flaw detection circuit 51 is connected at its input side to a transmission control circuit 61 via a wiring r, and is connected at its output side to each oscillator 11a via the wirings m. The transmission flaw detection circuit 51 applies a pulse voltage at a predetermined timing to each oscillator 11a of the ultrasonic transmission probe 11 on the basis of a control signal from the transmission control circuit 61.

The reception flaw detection circuit 52 is connected at its input side to each oscillator 21a of the ultrasonic reception probe 21 via the wirings n, and is connected at its output side to a reception control circuit 62 via a wiring s. The reception flaw detection circuit 52 fetches an electric signal from each oscillator 21a of the ultrasonic reception probe 21, and outputs the electric signal as predetermined data to the reception control circuit 62.

The flaw detector control device 60 includes, though not illustrated, electric circuits such as CPU, ROM, RAM, and various interfaces, and reads the programs stored in the ROM and develops them into the RAM so that the CPU performs various processing. As illustrated in FIG. 2, the flaw detector control device 60 includes the transmission control circuit 61 connected to the transmission flaw detection circuit 51, and the reception control circuit 62 connected to the reception flaw detection circuit 52.

The transmission control circuit 61 outputs a control signal for oscillating each oscillator 11a at a predetermined timing to the transmission flaw detection circuit 51. In the example illustrated in FIG. 2, the transmission control circuit 61 oscillates each oscillator 11a arranged in line, which is farther away from the oscillator 11a around the center, at an earlier timing. Thereby, an ultrasonic wave (spherical wave) occurring along with oscillation of each oscillator 11a converges toward the focus. The oscillation timing at each oscillator 11a is controlled such that the focus is positioned at a predetermined inspection site Q (see FIG. 3) on the pipe G. Thereby, the damage on the pipe G can be detected at high sensitivity. The "inspection site Q" is a site where the presence of damage is to be inspected on the pipe G.

The reception control circuit 62 illustrated in FIG. 2 has a function of inspecting the present of damage on the pipe G on the basis of a reception result of the ultrasonic reception probe 21. The reception control circuit 62 has a function of outputting a state of the inspection site Q on the pipe G as image data to a display device (not illustrated).

Figure 3:
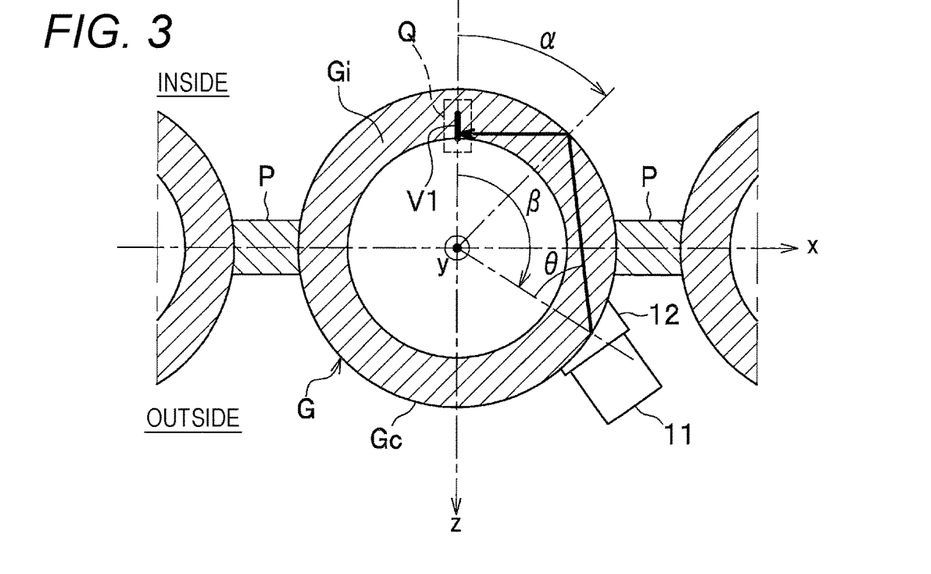
FIG. 3 is a cross-section view along the line II-II in FIG. 1 of the piping inspection apparatus according to the first embodiment of the present invention.

FIG. 3 is a cross-section view along the line II-II in FIG. 1 of the piping inspection apparatus 100 according to the first embodiment. "Inside" illustrated in FIG. 3 indicates being closer to the boiler furnace (not illustrated) than to the water-wall W (see FIG. 1), and "outside" indicates to be farther away from the boiler furnace.

As illustrated in FIG. 3, it is assumed that the center axis of the pipe G is y-axis, a line perpendicular to the wall of the film plate P and crossing with the y-axis is z-axis, and a line perpendicular to the y-axis and the z-axis is x-axis. A bold arrow illustrated in FIG. 3 indicates a route through which an ultrasonic wave (high-directivity ultrasonic beam) propagates in the thick part Gi of the pipe G.

Other pipe (not illustrated) is installed around the water-wall W inside the water-wall W (in the depth side in FIG. 1) in many cases, and ash is attached inside the water-wall W even when the boiler furnace (not illustrated) is stopped. Thus, the pipe G inside the water-wall W is difficult to inspect by an inspector. Thus, according to the first embodiment, the ultrasonic transmission probe 11 and the ultrasonic reception probe 21 are arranged outside the water-wall W (closer to the lower side in FIG. 1 or on the positive z-axis side in FIG. 3) to inspect the pipe G.

The wedge 12 illustrated in FIG. 3 is a member present between the ultrasonic transmission probe 11 and the pipe G, and is fixed on the ultrasonic transmission probe 11 by metal part or screw. An ultrasonic wave from each oscillator 11a (see FIG. 2) of the ultrasonic transmission probe 11 is incident into the pipe G via the wedge 12. The wedge 12 is made of epoxy resin or polystyrene resin, and has a function of stabilizing an installation angle of the ultrasonic transmission probe 11 and enhancing a transmission efficiency of an ultrasonic wave. A face of the wedge 12 contacting with the outer peripheral face of the pipe G is formed according to a curvature of the outer peripheral face of the pipe G (or such that a gap is not present between the wedge 12 and the pipe G).

Figure 4:
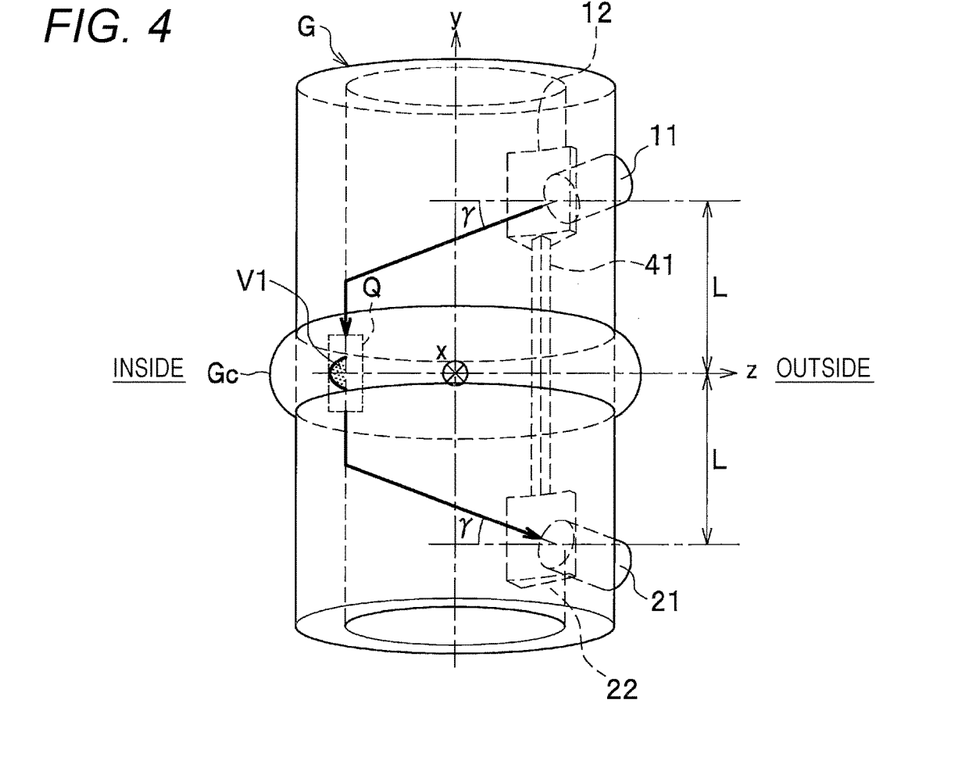
FIG. 4 is an explanatory diagram of a pipe, an ultrasonic transmission probe, an ultrasonic reception probe, and the like in the piping inspection apparatus according to the first embodiment of the present invention viewed in the negative x-axis direction.

FIG. 4 is an explanatory diagram of the pipe G, the ultrasonic transmission probe 11, the ultrasonic reception probe 21, and the like viewed in the negative x-axis direction. The film plate P (see FIG. 3) is not illustrated in FIG. 4.

The wedge 22 illustrated in FIG. 4 is a member present between the ultrasonic reception probe 21 and the pipe G, and is fixed on the ultrasonic reception probe 21 by metal part or screw. An ultrasonic wave is incident into each oscillator 21a (see FIG. 2) of the ultrasonic reception probe 21 via the wedge 22.

The holding unit 41 is a member for holding a distance (=2 L) between the wedge 12 and the wedge 22, and has a rod shape in the example illustrated in FIG. 4. The holding unit 41 is fixed at one end on the wedge 12 and is fixed at the other end on the wedge 22.

When the inspector inspects the presence of damage on the pipe G, a contact medium such as water, oil, or glycerin paste is applied on the faces of the wedges 12 and 22 on the pipe G. The inspector performs the ultrasonic testing while supporting the holding unit 41 or the like by hand.

<Arrangement of Ultrasonic Transmission Probe and Ultrasonic Reception Probe>

The description will be made below assuming that the inner peripheral face (particularly a position on the z-axis in FIG. 3) of the pipe G closer to (inside) the boiler furnace is an "inspection site Q" and an inspection is carried out as to whether an axial crack is present at the "inspection site Q."

In the example illustrated in FIGS. 3 and 4, an axial crack V1 is present on the z-axis on the inner peripheral face of the pipe G.

As illustrated in FIG. 3, the ultrasonic transmission probe 11 is arranged such that an ultrasonic wave transmitted from the ultrasonic transmission probe 11 toward the pipe G propagates in the thick part Gi of the pipe G, is reflected on the outer peripheral face of the pipe G once, and travels toward the inspection site Q on the pipe G.

An angle $\alpha$ illustrated in FIG. 3 indicates a position where an ultrasonic wave is reflected on the outer peripheral face of the pipe G in the circumferential direction with reference to the z-axis (0°). The angle $\alpha$ is set such that when an axial crack V1 is present at the inspection site Q, an ultrasonic wave reflected on the outer peripheral face of the pipe G is incident into the axial crack V1 substantially perpendicularly in planar view. In other words, the angle $\alpha$ is set assuming that an axial crack V1 substantially parallel to a plane including the center axis (the y-axis) of the pipe G (the yz plane in FIG. 3) is present on the inner peripheral face of the pipe G.

The angle $\alpha$ is preferably between 35° and 55°. This is because when the angle $\alpha$ is within the range, an ultrasonic wave is incident into the axial crack V1 substantially perpendicularly in planar view. Thereby, the reflection intensity of the ultrasonic wave at the axial crack V1 can be further enhanced than when an ultrasonic wave is incident into the axial crack V1 in other direction.

An angle $\beta$ illustrated in FIG. 3 indicates an installation position of the wedge 12, 22 in the circumferential direction with reference to the z-axis (0°). The angle $\beta$ of k is set such that an ultrasonic wave is reflected at the angle $\alpha$ on the other peripheral face of the pipe G. It is preferable that the wedges 12, 22 are arranged at an angle between 90° and 135° and more preferably between 105° and 135° on the pipe G in the circumferential direction with reference to the yz plane including the inspection site Q and the center axis (the y-axis) of the pipe G. This is because an ultrasonic wave reflected on the outer peripheral face of the pipe G is incident into the axial crack V1 substantially perpendicularly in planar view and an ultrasonic wave reflected on the axial crack V1 travels toward the ultrasonic reception probe 21 via the wedge 22.

A refraction angle $\theta$ illustrated in FIG. 3 is a refraction angle of an ultrasonic wave on the interface between the wedge 12 and the pipe G. The refraction angle $\theta$ is preferably between 35° and 45°. This is because an ultrasonic wave reflected on the outer peripheral face of the pipe G is incident into the axial crack V1 substantially perpendicularly in planar view.

An angle $\gamma$ illustrated in FIG. 4 is formed between a plane perpendicular to the center axis (the y-axis) of the pipe G and a route of an ultrasonic wave transmitted from the ultrasonic transmission probe 11. The angle $\gamma$ is set as needed in consideration of the inner diameter and outer diameter of the pipe G, a thickness of the circumferential welded part Gc, an interference of an ultrasonic wave on the film plate P (see FIG. 3), and the like. The angle $\gamma$ is preferably between 20° and 70°. This is because an ultrasonic wave reflected on the outer peripheral face of the pipe G travels toward the inspection site Q in side view. The wedges 12 and 22 are configured such that the angles $\theta$, $\alpha$, $\beta$, and $\gamma$ are kept while the wedges 12 and 22 are pressed onto the pipe G.

As illustrated in FIG. 4, the ultrasonic transmission probe 11 and the ultrasonic reception probe 21 are arranged on one side and the other side of the circumferential welded part Gc including the inspection site Q in the axial direction (in the y-axis direction) of the pipe G, respectively. More specifically, the ultrasonic reception probe 21 is arranged to be symmetrical to the ultrasonic transmission probe 11 with reference to the xz plane including the inspection site Q and perpendicular to the center axis (the y-axis) of the pipe G.

Thus, the angles $\theta$, $\alpha$, $\beta$, and $\gamma$ have substantially the same values on the transmission side and the reception side of an ultrasonic wave. Consequently, a route of an ultrasonic wave from the ultrasonic transmission probe 11 toward the axial crack V1 and a route of an ultrasonic wave reflected on the axial crack V1 and traveling toward the ultrasonic reception probe 21 appear to be overlapped in planar view (see FIG. 3). That is, the ultrasonic reception probe 21 is arranged to be symmetrical to the ultrasonic transmission probe 11 with reference to the xz plane, and thus the routes are symmetrical to each other with reference to the xz plane (see FIG. 4).

It is preferable that the holding unit 41 illustrated in FIG. 4 can adjust a distance between the wedge 12 and the wedge 22 (=2 L). For example, the holding unit 41 may include two mutually-engaged rails (not illustrated) and screws (not illustrated) for holding the full-length of the rails. With the configuration, the wedge 12 is fixed on one rail and the wedge 22 is fixed on the other rail. The holding unit 41 can adjust the length in this way, thereby performing the ultrasonic testing on another pipe (not illustrated) with different inner diameter in the configuration illustrated in FIGS. 3 and 4.

<Processing by Flaw Detector Control Device>

Figure 5:
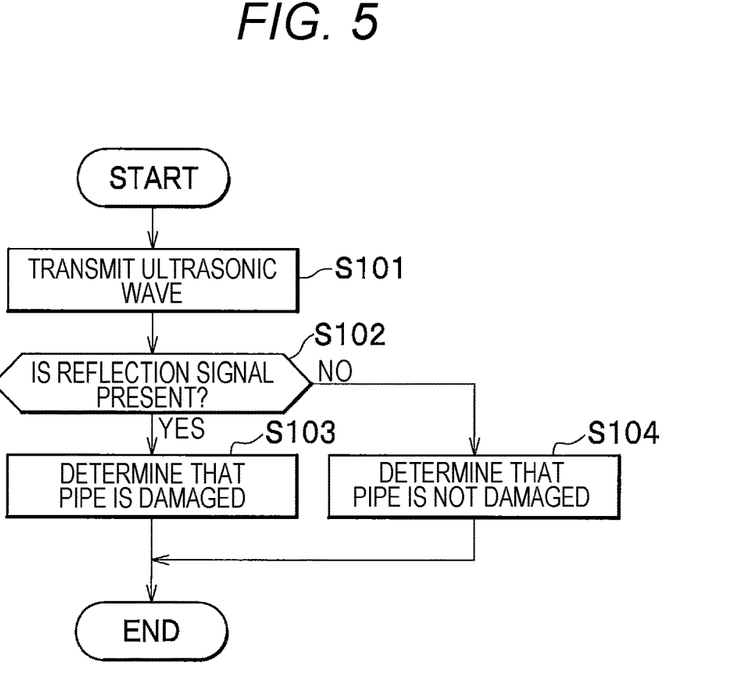
FIG. 5 is a flowchart of the processing performed by a flaw detector control device provided in the piping inspection apparatus according to the first embodiment of the present invention.

FIG. 5 is a flowchart of the processing performed by the flaw detector control device 60.

It is assumed that the ultrasonic transmission probe 11 and the ultrasonic reception probe 21 are arranged as illustrated in FIGS. 3 and 4 on "START" time of FIG. 5. When the inspector presses the start button (not illustrated) of the flaw detector control device 60 (see FIG. 2), a series of processing illustrated in FIG. 5 are started.

In step S101, the flaw detector control device 60 transmits an ultrasonic wave from the ultrasonic transmission probe 11 via the transmission control circuit 61 (see FIG. 2). The ultrasonic wave transmitted from the ultrasonic transmission probe 11 is refracted on the interface between the ultrasonic transmission probe 11 and the wedge 12, is then reflected on the outer peripheral face of the pipe G, and travels toward the inspection site Q as described above.

If an axial crack V1 is present at the inspection site Q, the ultrasonic wave is reflected on the axial crack V1, is further reflected on the outer peripheral face of the pipe G, and travels toward the ultrasonic reception probe 21.

Further, if an axial crack V1 is not present at the inspection site Q, the ultrasonic wave is repeatedly reflected on the outer peripheral face or the inner peripheral face of the pipe G, and attenuates. Consequently, the ultrasonic wave is not received by the ultrasonic reception probe 21 or the slight ultrasonic wave due to back bead welding inside the pipe is received.

In step S102, the flaw detector control device 60 determines whether a predetermined reflection signal is present. That is, in step S102, the flaw detector control device 60 determines whether the intensity of the reflection signal from the ultrasonic flaw detector 50 (see FIG. 2) is a predetermined threshold or more. The "predetermined threshold" is a determination reference as to whether an axial crack V1 is present on the inner peripheral face of the pipe G, and is previously set. In step S102, when the predetermined reflection signal is present (S102: Yes), the processing of the flaw detector control device 60 proceeds to step S103.

In step S103, the flaw detector control device 60 determines that the pipe G is damaged. That is, the flaw detector control device 60 determines that the axial crack V1 (damage) is present on the inner peripheral face of the pipe G. In this case, the circumferential welded part Gc is repaired or the pipe G is replaced.

On the other hand, in step S102, when the predetermined reflection signal is not present (S102: No), the processing of the flaw detector control device 60 proceeds to step S104.

In step S104, the flaw detector control device 60 determines that the pipe G is not damaged. That is, the flaw detector control device 60 determines that the axial crack V1 (damage) is not present on the inner peripheral face of the pipe G.

After performing the processing in step S103 or S104, the flaw detector control device 60 terminates the processing (END). The determination result of the flaw detector control device 60 or the images acquired in the ultrasonic testing are displayed on the display device (not illustrated) such as display.

A circumferential position of the axial crack V1 is not previously specified, and thus the inspector circumferentially scans the ultrasonic transmission probe 11 and the ultrasonic reception probe 21 on the pipe G thereby to confirm the presence of a reflection signal. As described above, the wedges 12 and 22 are configured such that the angles $\alpha$, $\beta$, $\gamma$, and $\theta$ are kept, and the distance between the wedges 12 and 22 is held by the holding unit 41. Thus, the inspector circumferentially scans the pipe G while pressing the wedges 12 and 22 onto the pipe G, thereby inspecting the presence of damage with high accuracy at each part of the pipe G in the circumferential direction.

Additionally, for an axial crack on the inner peripheral face of the pipe G outside the boiler furnace (not illustrated), the ultrasonic transmission probe 11 and the ultrasonic reception probe 21 are arranged outside the boiler furnace and the wedges (not illustrated) may be configured such that an ultrasonic wave travels toward the inspection site (is not reflected on the outer peripheral face of the pipe G), for example.

<Effects>

According to the first embodiment, the ultrasonic transmission probe 11 and the ultrasonic reception probe 21 are arranged on one side and the other side of the circumferential welded part Gc in the axial direction, respectively. Thereby, the presence of an axial crack V1 at the circumferential welded part Gc can be inspected without pressing the wedges 12 and 22 onto the circumferential welded part Gc. If a wedge is pressed onto non-uniform weld reinforcement of the circumferential welded part Gc, a gap is caused between the wedge and the circumferential welded part Gc, and thus an ultrasonic wave attenuates in the gap. For example, with the conventional technique described in JP 2014-81376 A, when a probe is arranged on weld reinforcement of the circumferential welded part Gc, the probe is unstable and an ultrasonic wave is likely to attenuate due to a gap between the wedge and the probe. To the contrary, according to the first embodiment, the ultrasonic testing is performed while the wedges 12 and 22 are tightly attached on the pipe G via a contact medium such as glycerin, thereby restricting attenuation of an ultrasonic wave.

The ultrasonic testing can be performed farther away from (outside) the boiler furnace even when an obstacle such as the water-wall W (see FIG. 1) is present and the ultrasonic testing is difficult to perform closer to (inside) the boiler furnace. Thereby, it is possible to appropriately and easily inspect whether damage is present on the inner peripheral face of the pipe G closer to the boiler furnace.

The ultrasonic transmission probe 11 is arranged at the angles α, β, γ, and θ, and thus an ultrasonic wave is incident into the axial crack V1 substantially perpendicularly in planar view (see FIG. 3). Thereby, the reflection intensity of the ultrasonic wave at the axial crack V1 takes a relatively high value, thereby detecting the axial crack V1 at high sensitivity.

The ultrasonic reception probe 21 is arranged to be symmetrical to the ultrasonic transmission probe 11 with reference to the xz plane. Thereby, the ultrasonic wave reflected on the axial crack V1 can be received by the ultrasonic reception probe 21 at high sensitivity.

Further, according to the first embodiment, the ultrasonic transmission probe 11 and the ultrasonic reception probe 21 employ an ultrasonic array probe. Thereby, a timing to oscillate the oscillators 11a can be electronically controlled, an ultrasonic wave can be converged at any position, and an ultrasonic wave can propagate in any direction. Further, the sector scanning method for scanning an ultrasonic wave in a fan-like shape is employed so that a position of a focus of an ultrasonic wave can be adjusted in consideration of an error in deformation even when the circumferential welded part Gc is deformed to be flattened or the like. Thereby, the axial crack V1 on the pipe G can be detected with high accuracy.

Second Embodiment

A second embodiment is different from the first embodiment in that the ultrasonic transmission probe 11 and an ultrasonic reception probe 31 are arranged to be symmetrical to each other with reference to the yz plane in order to inspect the presence of a circumferential crack (which will be called "circumferential crack V2" below: see FIG. 6) on the inner peripheral face of the pipe G. Other points are similar to the first embodiment. Thus, only the difference from the first embodiment will be described and the repeated description will be omitted.

Figure 6:
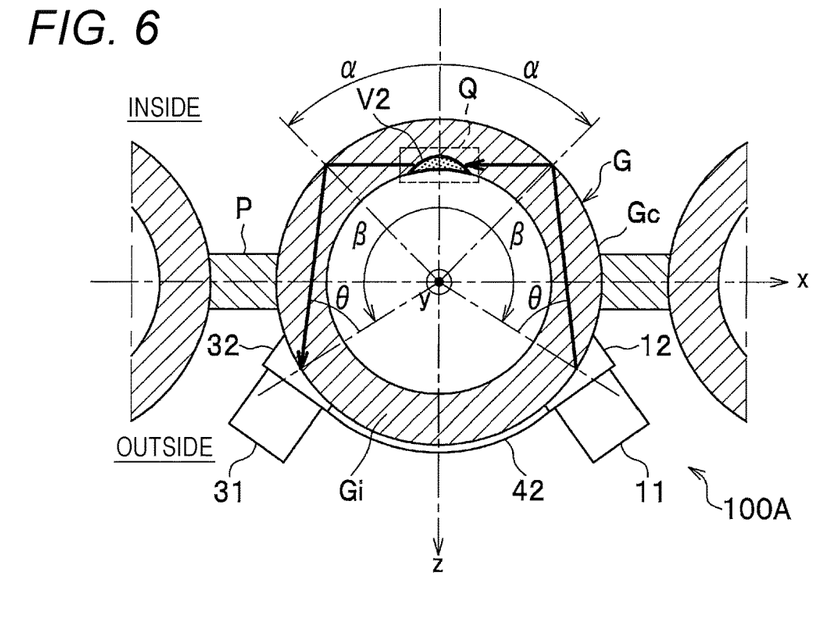
FIG. 6 is a transverse cross-section view including an ultrasonic transmission probe and an ultrasonic reception probe in a piping inspection apparatus according to a second embodiment of the present invention.

FIG. 6 is a transverse cross-section view including the ultrasonic transmission probe 11 and the ultrasonic reception probe 31 in a piping inspection apparatus 100A according to the second embodiment.

The piping inspection apparatus 100A illustrated in FIG. 6 includes the ultrasonic transmission probe 11, the ultrasonic reception probe 31, wedges 12, 32, a holding unit 42, the ultrasonic flaw detector 50, and the flaw detector control device 60. The configurations of the ultrasonic flaw detector 50 and the flaw detector control device 60 are similar to those in the first embodiment (see FIG. 2).

The ultrasonic transmission probe 11 is arranged such that an ultrasonic wave transmitted from the ultrasonic transmission probe 11 toward the pipe G propagates in the thick part Gi of the pipe G, is reflected on the outer peripheral face of the pipe G once, and travels toward the inspection site Q on the pipe G. An installation angle (or the angles θ, α, β, and γ) of the ultrasonic transmission probe 11 relative to the inspection site Q is similar to the installation angle of the ultrasonic transmission probe 11 described in the first embodiment (see FIGS. 3 and 4). Thus, a route through which an ultrasonic wave from the ultrasonic transmission probe 11 toward the inspection site Q propagates is also similar to that in the first embodiment (see FIGS. 3 and 4).

The ultrasonic reception probe 31 is arranged to be symmetrical to the ultrasonic transmission probe 11 with reference to the yz plane including the inspection site Q and the center axis (the y-axis) of the pipe G. The angles α, β, θ, and γ (see FIG. 7) indicating an installation angle of the ultrasonic reception probe 31 are substantially the same as the angles α, β, θ, and γ (see FIG. 7) indicating the installation angle of the ultrasonic transmission probe 11.

The holding unit 42 is a member for holding a distance between the wedge 12 and the wedge 32, and has an arc shape in planar view in the example illustrated in FIG. 6. It is preferable that the holding unit 42 can adjust the distance between the wedge 12 and the wedge 32. This is because the ultrasonic testing can be performed on another pipe (not illustrated) with different inner diameter in the configuration illustrated in FIGS. 6 and 7.

Figure 7:
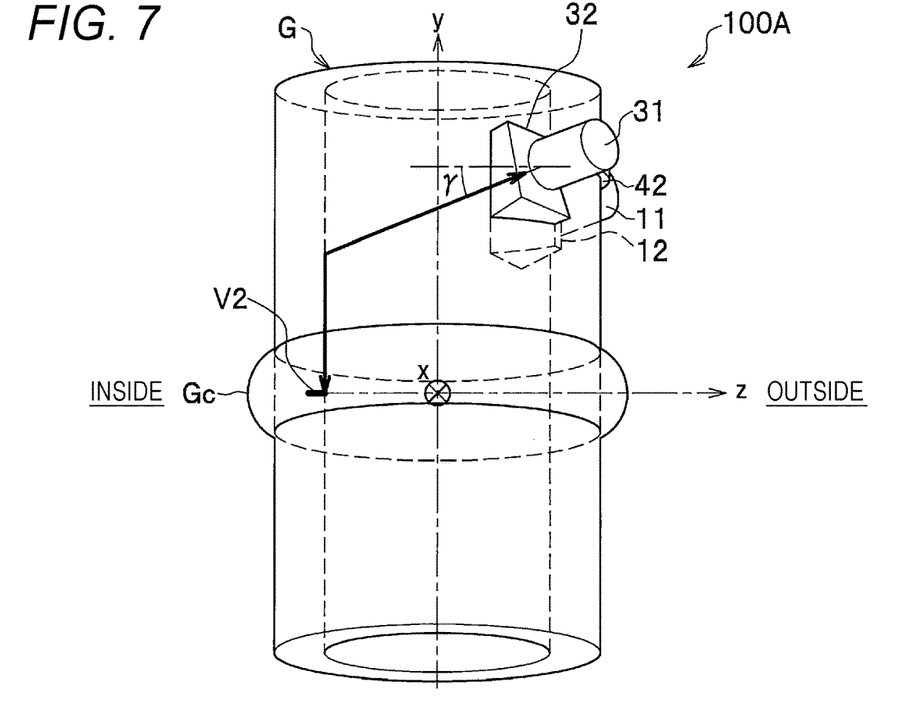
FIG. 7 is an explanatory diagram of a pipe, the ultrasonic transmission probe, the ultrasonic reception probe, and the like in the piping inspection apparatus according to the second embodiment of the present invention viewed in the negative x-axis direction.

FIG. 7 is an explanatory diagram of the pipe G, the ultrasonic transmission probe 11, the ultrasonic reception probe 31, and the like viewed in the negative x-axis direction.

As illustrated in FIG. 7, a route of an ultrasonic wave from the ultrasonic transmission probe 11 toward the circumferential crack V2 and a route of an ultrasonic wave reflected on the circumferential crack V2 and traveling toward the ultrasonic reception probe 31 appear to be overlapped in side view. That is, the routes are symmetrical to each other with reference to the yz plane. A distance between the ultrasonic transmission probe 11 and the xz plane (which is also a distance between the ultrasonic reception probe 31 and the xz plane) is set as needed on the basis of the inner diameter, the outer diameter, and the like of the pipe G.

The processing performed by the flaw detector control device 60 are similar to those in the first embodiment (see FIG. 5), and thus the description thereof will be omitted.

<Effects>

According to the second embodiment, the ultrasonic transmission probe 11 and the ultrasonic reception probe 31 are arranged on one side (upward) of the circumferential welded part Gc in the axial direction. Thereby, the presence of a circumferential crack V2 on the circumferential welded part Gc can be detected without pressing the wedges 12 and 32 onto the circumferential welded part Gc.

Further, the ultrasonic transmission probe 11 is arranged at the angles α, β, γ, and θ so that an ultrasonic wave is incident into the circumferential crack V2 substantially perpendicularly in side view (see FIG. 7). Thereby, the reflection intensity of the ultrasonic wave at the circumferential crack V2 is relatively high, and thus the circumferential crack V2 can be detected at high sensitivity.

Third Embodiment

A third embodiment is different from the first embodiment in that a circumferential position of an axial crack V3 (see FIG. 8) is specified on the basis of a time from transmission to reception of an ultrasonic wave. The arrangement of the ultrasonic transmission probe 11 and the ultrasonic reception probe 21 is similar to that in the first embodiment (see FIGS. 3 and 4). Thus, only the difference from the first embodiment will be described, and the repeated description will be omitted.

Figure 8:
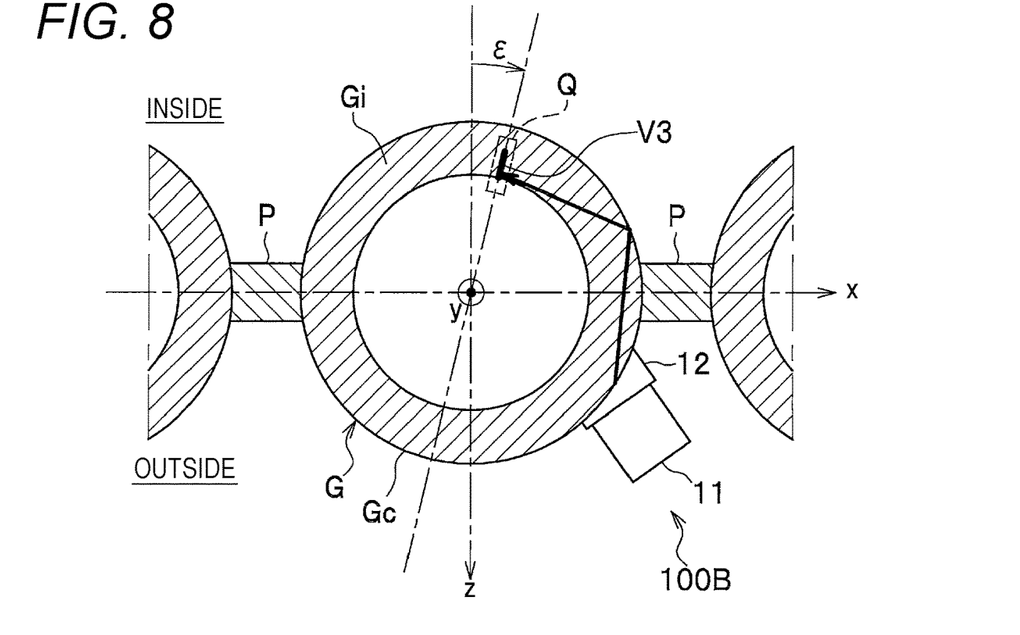
FIG. 8 is a transverse cross-section view of an ultrasonic transmission probe and an ultrasonic reception probe arranged on one side in the yz plane in a piping inspection apparatus according to a third embodiment of the present invention.

FIG. 8 is a transverse cross-section view of the ultrasonic transmission probe 11 and the ultrasonic reception probe 21 on one side in the yz plane in a piping inspection apparatus 100B according to the third embodiment.

The ultrasonic reception probe 21 is not illustrated in FIG. 8, but the ultrasonic reception probe 21 is positioned immediately below the ultrasonic transmission probe 11. In the example illustrated in FIG. 8, an axial crack V3 is present at an angle ε in the circumferential direction with reference to the z-axis.

As illustrated in FIG. 8, the flaw detector control device 60 inspects the presence of an axial crack V3 while the ultrasonic transmission probe 11 and the ultrasonic reception probe 21 (not illustrated) are arranged on one side (on the right side in the Figure) in the yz plane including the inspection site Q and the center axis (the y-axis) of the pipe G. The flaw detector control device 60 measures a time t1 after the ultrasonic transmission probe 11 transmits an ultrasonic wave until the ultrasonic reception probe 21 receives the ultrasonic wave.

Figure 9:
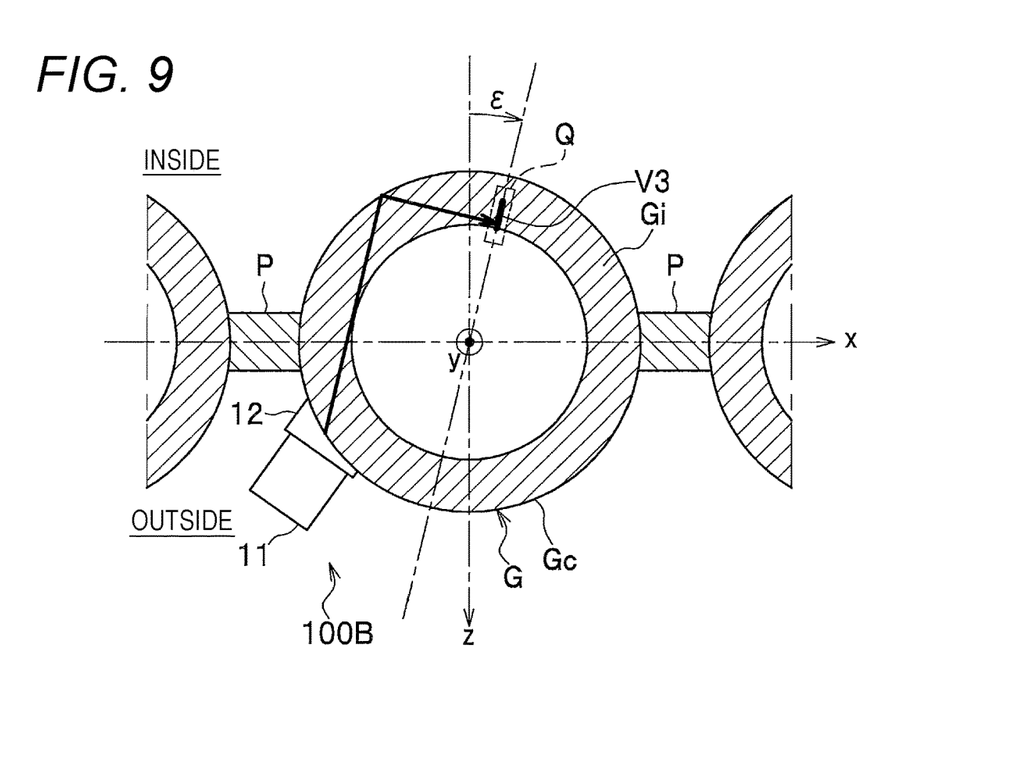
FIG. 9 is a transverse cross-section view of the ultrasonic transmission probe and the ultrasonic reception probe arranged on the other side in the yz plane in the piping inspection apparatus according to the third embodiment of the present invention.

FIG. 9 is a transverse cross-section view of the ultrasonic transmission probe 11 and the ultrasonic reception probe 21 arranged on the other side in the yz plane.

As illustrated in FIG. 9, the flaw detector control device 60 inspects the presence of an axial crack V3 while the ultrasonic transmission probe 11 and the ultrasonic reception probe 21 (not illustrated) are arranged on the other side (on the left side in the Figure) in the yz plane including the inspection site Q and the center axis (the y-axis) of the pipe G. The flaw detector control device 60 measures a time t2 after the ultrasonic transmission probe 11 transmits an ultrasonic wave until the ultrasonic reception probe 21 receives the ultrasonic wave.

In the example illustrated in FIG. 9, the position of the axial crack V3 is closer to one side (the right side in the Figure) in the yz plane, and thus the time t2 is longer than the time t1. As a ratio of the time t2 to the time t1 is larger, the circumferential angle ε is larger. The flaw detector control device 60 specifies the circumferential position (or the angle ε) of the damage on the pipe G on the basis of the ratio between the time t1 and the time t2.

<Effects>

According to the third embodiment, a circumferential position (the angle ε) of the axial crack V3 can be specified on the basis of the ratio between the time t1 and the time t2. A position of the axial crack V3 is specified in this way, thereby accurately specifying the defect position and preventing erroneous determination.

Fourth Embodiment

A fourth embodiment is configured such that the ultrasonic reception probe 31 (see FIG. 10) arranged to be symmetrical to the ultrasonic transmission probe 11 with reference to the yz plane is added to the configuration of the first embodiment thereby to inspect both axial crack and circumferential crack on the pipe G. Other points (such as arrangement of the ultrasonic transmission probe 11 and the ultrasonic reception probe 21) are similar to the first embodiment. Thus, only the difference from the first embodiment will be described and the repeated description will be omitted.

Figure 10:
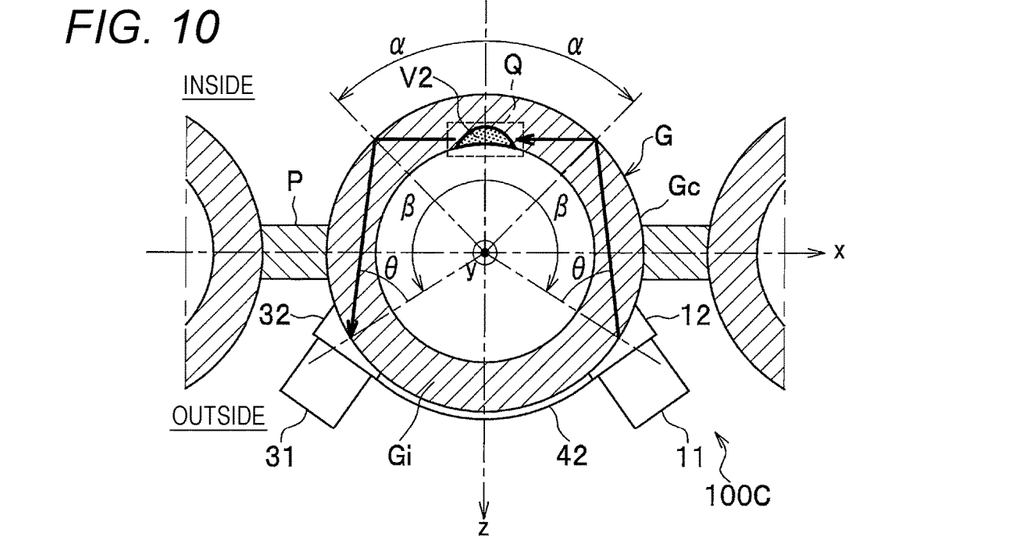
FIG. 10 is a transverse cross-section view including an ultrasonic transmission probe and an ultrasonic reception probe in a piping inspection apparatus according to a fourth embodiment of the present invention.

FIG. 10 is a transverse cross-section view including the ultrasonic transmission probe 11 and the ultrasonic reception probe 31 in a piping inspection apparatus 100C according to the fourth embodiment.

FIG. 10 illustrates that a circumferential crack V2 is present at the inspection site Q, but an axial crack may be present at the inspection site Q in some cases.

The piping inspection apparatus 100C illustrated in FIG. 10 includes the ultrasonic transmission probe 11, the wedge 12 (transmission wedge), the ultrasonic reception probe 21 (first ultrasonic reception probe: see FIG. 11), the wedge 22 (first reception wedge: see FIG. 11), the ultrasonic reception probe 31 (second ultrasonic reception probe), and the wedge 32 (second reception wedge). The piping inspection apparatus 100C further includes the holding unit 41 (first holding unit), the holding unit 42 (second holding unit), the ultrasonic flaw detector 50, and the flaw detector control device 60 in addition to the above components. The configurations of the ultrasonic flaw detector 50 and the flaw detector control device 60 are similar to those in the first embodiment (see FIG. 2).

The ultrasonic transmission probe 11 is arranged on the pipe G via the wedge 12 such that an ultrasonic wave transmitted from the ultrasonic transmission probe 11 toward the pipe G propagates in the thick part Gi of the pipe G, is reflected on the outer peripheral face of the pipe G once, and travels toward the inspection site Q on the pipe G.

The wedge 12 is a member present between the ultrasonic transmission probe 11 and the pipe G, and is fixed on the ultrasonic transmission probe 11.

The ultrasonic reception probe 31 is directed for detecting a circumferential crack on the inner peripheral face of the pipe G, and is arranged on the pipe G via the wedge 32. As illustrated in FIG. 10, the ultrasonic reception probe 31 is arranged to be symmetrical to the ultrasonic transmission probe 11 with reference to the yz plane including the inspection site Q and the center axis (the y-axis) of the pipe G.

The wedge 32 is a member present between the ultrasonic reception probe 31 and the pipe G, and is fixed on the ultrasonic reception probe 31.

The holding unit 42 is a member for holding a distance between the wedge 12 and the wedge 32, and has an arc shape in planar view. The holding unit 42 is fixed at one end on the wedge 12 and is fixed at the other end on the wedge 32.

Figure 11:
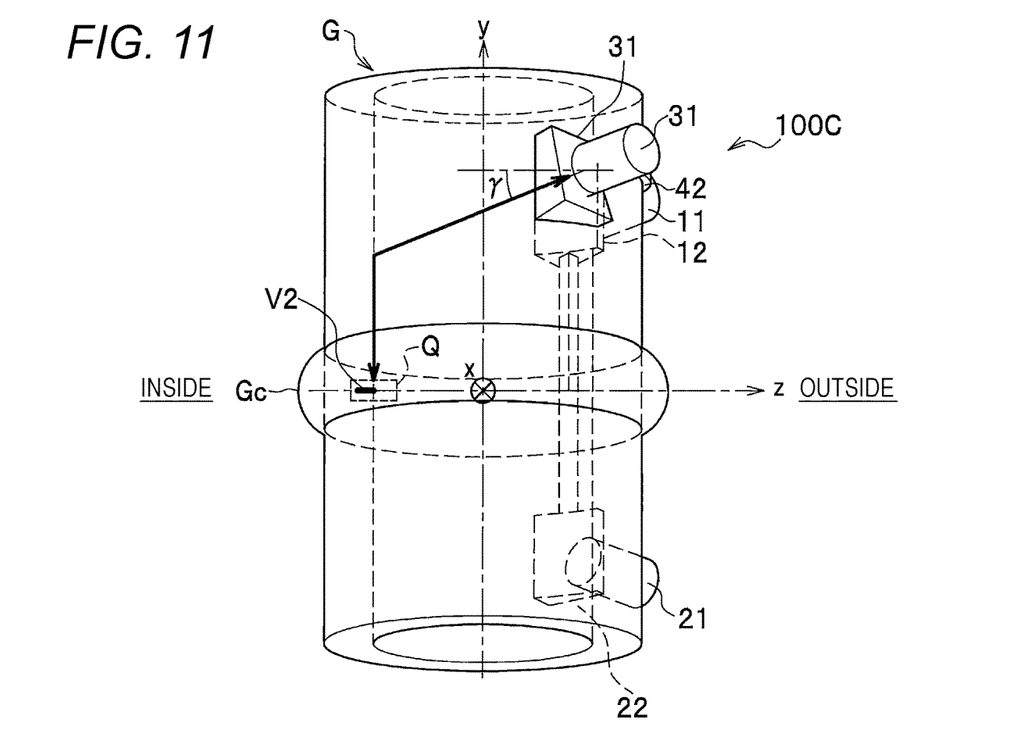
FIG. 11 is an explanatory diagram of a pipe, the ultrasonic transmission probe, the ultrasonic reception probe, and the like in the piping inspection apparatus according to the fourth embodiment of the present invention viewed in the negative x-axis direction.

FIG. 11 is an explanatory diagram of the pipe G, the ultrasonic transmission probe 11, the ultrasonic reception probes 21, 31, and the like viewed in the negative x-axis direction.

The ultrasonic reception probe 21 is directed for detecting an axial crack on the inner peripheral face of the pipe G, and is arranged on the pipe G via the wedge 22. As illustrated in FIG. 11, the ultrasonic reception probe 21 is arranged to be symmetrical to the ultrasonic transmission probe 11 with reference to the xz plane including the inspection site Q and perpendicular to the center axis (the y-axis) of the pipe G.

The wedge 22 is a member present between the ultrasonic reception probe 21 and the pipe G, and is fixed on the ultrasonic reception probe 21.

The holding unit 41 is a member for holding a distance between the wedge 12 and the wedge 22, and has a rod shape in the example illustrated in FIG. 11. The holding unit 41 is fixed at one end on the wedge 12 and is fixed at the other end on the wedge 22.

It is preferable that the holding unit 41 can adjust a distance between the wedge 12 and the wedge 22. Similarly, it is preferable that the holding unit 42 illustrated in FIG. 10 can adjust a distance between the wedge 12 and the wedge 32. This is because the ultrasonic testing can be performed on another pipe (not illustrated) with different inner diameter and outer diameter in the configuration illustrated in FIGS. 10 and 11.

<Processing by Flaw Detector Control Device>

Figure 12:
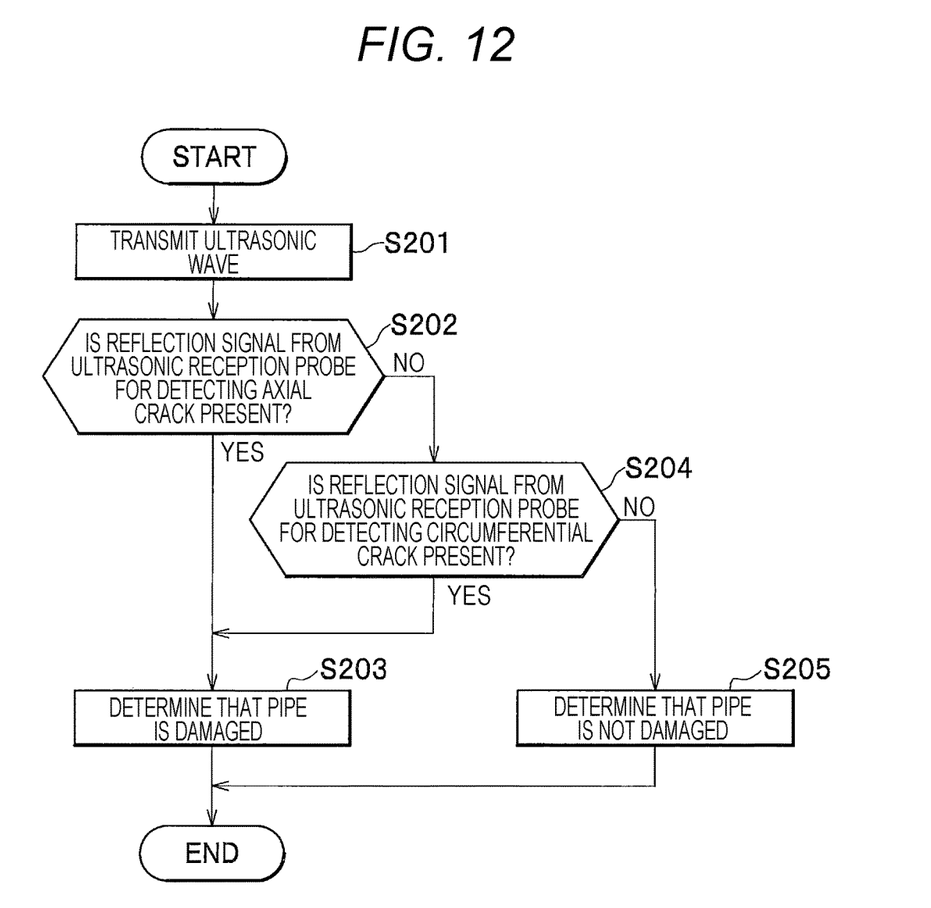
FIG. 12 is a flowchart of the processing performed by the flaw detector control device provided in the piping inspection apparatus according to the fourth embodiment of the present invention.

FIG. 12 is a flowchart of the processing performed by the flaw detector control device 60.

In step S201, the flaw detector control device 60 transmits an ultrasonic wave from the ultrasonic transmission probe 11.

In step S202, the flaw detector control device 60 determines whether a predetermined reflection signal from the ultrasonic reception probe 21 for detecting axial crack is present. When the predetermined reflection signal from the ultrasonic reception probe 21 is present (S202: Yes), the processing of the flaw detector control device 60 proceeds to step S203.

In step S203, the flaw detector control device 60 determines that the pipe G is damaged. That is, the flaw detector control device 60 determines that an axial crack (damage) is present on the inner peripheral face of the pipe G.

In step S202, when the predetermined reflection signal is not present (S202: No), the processing of the flaw detector control device 60 proceeds to step S204.

In step S204, the flaw detector control device 60 determines whether a predetermined reflection signal from the ultrasonic reception probe 31 for detecting circumferential crack is present. When the predetermined reflection signal from the ultrasonic reception probe 31 is present (S204: Yes), in step S203, the flaw detector control device 60 determines that the pipe G is damaged. That is, the flaw detector control device 60 determines that a circumferential crack (damage) is present on the inner peripheral face of the pipe G.

In step S204, when the predetermined reflection signal is not present (S204: No), the processing of the flaw detector control device 60 proceeds to step S205.

In step S205, the flaw detector control device 60 determines that the pipe G is not damaged. That is, the flaw detector control device 60 determines that neither axial crack (damage) nor circumferential crack (damage) is present on the inner peripheral face of the pipe G.

After performing the processing in step S203 or S205, the flaw detector control device 60 terminates the series of processing (END).

<Effects>

According to the fourth embodiment, the presence of an axial crack can be inspected by use of the ultrasonic transmission probe 11 and the ultrasonic reception probe 21, and the presence of a circumferential crack can be inspected by use of the ultrasonic transmission probe 11 and the ultrasonic reception probe 31. The distance between the wedges 12 and 22 can be held by the holding unit 41 and the distance between the wedges 12 and 32 can be held by the holding unit 42. Thus, the inspector has only to move the ultrasonic transmission probe 11 or the ultrasonic reception probes 21, 31 axially or circumferentially while bringing the holding units 41 and 42 by hand, thereby alleviating the working loads on the inspector.

<Variants>

The piping inspection apparatus 100 and the like according to the present invention have been described above by way of the embodiments, but the present invention is not limited thereto and can be variously changed.

For example, the description has been made assuming that the ultrasonic transmission probe 11 and the wedge 12 are separate parts and the ultrasonic reception probe 21 and the wedge 22 are separate parts according to the first embodiment (see FIG. 4), but the present invention is not limited thereto as described below.

Figure 13:
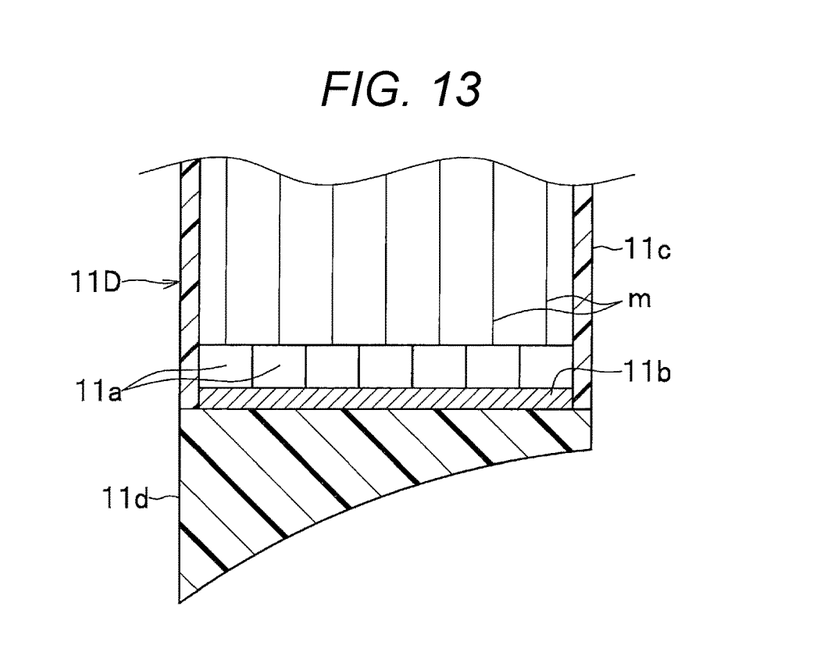
FIG. 13 is a longitudinal cross-section view of an ultrasonic transmission probe provided in a piping inspection apparatus according to a variant of the present invention.

FIG. 13 is a longitudinal cross-section view of an ultrasonic transmission probe 11D provided in a piping inspection apparatus according to a variant.

As illustrated in FIG. 13, the ultrasonic transmission probe 11D may include a wedge part 11d. The wedge part 11d is installed at the opening of a housing 11c housing the oscillators 11a and the acoustic adjustment layer 11b therein. Though not illustrated, the ultrasonic reception probe may similarly include a wedge part. The configuration illustrated in FIG. 13 may be added with the backing member or acoustic lens.

The description has been made assuming that an ultrasonic wave is reflected on the outer peripheral face of the pipe G once until the ultrasonic wave reaches the inspection site Q, but as described below, the ultrasonic transmission probe 11 and the like may be arranged such that an ultrasonic wave propagates in the thick part Gi of the pipe G and is at least reflected on the outer peripheral face of the pipe G (or is reflected on the inner peripheral face of the pipe G once or more times, or is reflected on the outer peripheral face of the pipe G once or more times).

Figure 14:
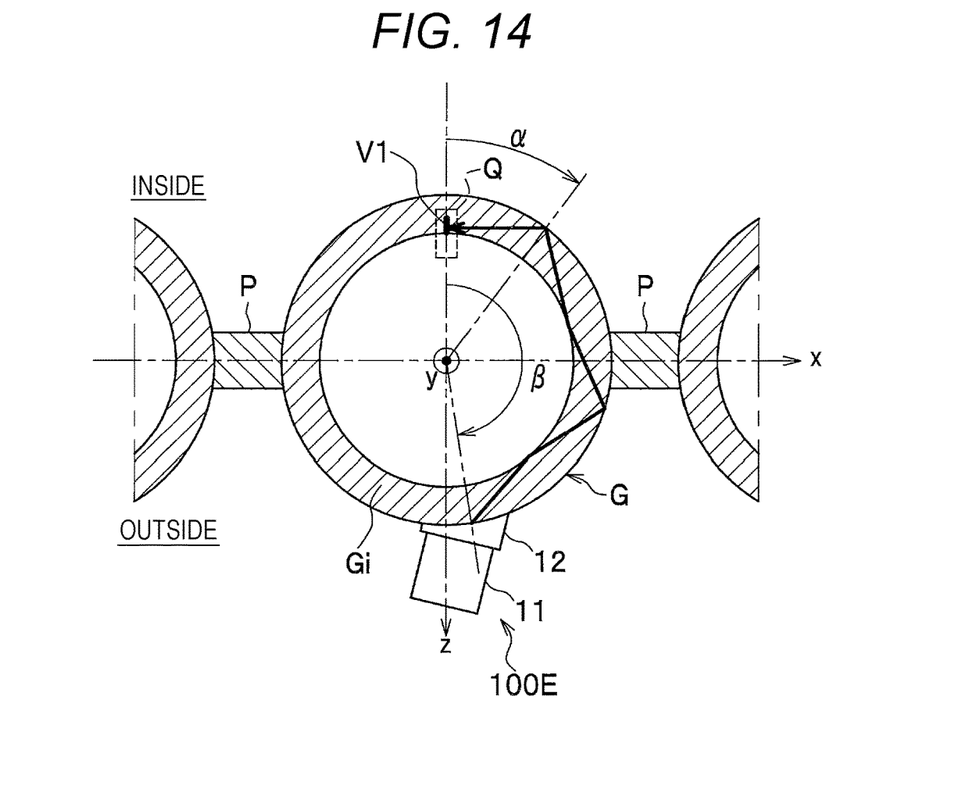
FIG. 14 is a transverse cross-section view illustrating a route of an ultrasonic wave transmitted from an ultrasonic transmission probe in a piping inspection apparatus according to another variant of the present invention.

FIG. 14 is a transverse cross-section view illustrating a route of an ultrasonic wave transmitted from the ultrasonic transmission probe 11 in a piping inspection apparatus 100E according to another variant.

For example, according to the first embodiment, when the pipe G is relatively thin, an ultrasonic wave may not be incident into the inspection site Q at an appropriate angle though it is reflected on the outer peripheral face of the pipe G once. In such a case, it is preferable to set the circumferential angle β indicating an installation position of the wedge 12, 22 to be larger. That is, it is preferable that an ultrasonic wave repeatedly reflected on the thick part Gi of the pipe G is further reflected at the angle α. Thereby, an ultrasonic wave is incident into the axial crack V1 substantially perpendicularly in planar view, thereby enhancing the reflection intensity of the ultrasonic wave at the axial crack V1.

In the example illustrated in FIG. 14, an ultrasonic wave refracted on the interface between the wedge 12 and the pipe G is sequentially reflected on the inner peripheral face, the outer peripheral face, the inner peripheral face, and the outer peripheral face of the pipe G, and travels toward the inspection site Q. A route of an ultrasonic wave reflected on the axial crack V1 at the inspection site Q and traveling toward the ultrasonic reception probe 21 is substantially the same as the route illustrated in FIG. 14 in planar view. The aforementioned contents can be applied to the second, third, and fourth embodiments.

The configuration in which the piping inspection apparatus 100 includes the holding unit 41 (see FIG. 4) has been described according to the first embodiment, but the holding unit 41 may be omitted and the inspector may perform the ultrasonic testing while bringing the wedges 12, 22 by hand. This is similarly applicable to the second, third, and fourth embodiments.

In the configuration of the first embodiment (see FIGS. 3 and 4), the ultrasonic reception probe 21 may be moved to be symmetrical to the ultrasonic transmission probe 11 with reference to the yz plane (see FIG. 6) and inspect the presence of a circumferential crack after inspecting the presence of an axial crack on the pipe G. Thereby, not only the presence of an axial crack but also the presence of a circumferential crack can be inspected. The ultrasonic transmission probe 11 may be moved to be symmetrical to the ultrasonic reception probe 21 with reference to the yz plane instead of moving the ultrasonic reception probe 21.

In the configuration of the second embodiment (see FIGS. 6 and 7), the ultrasonic reception probe 31 may be moved to be symmetrical to the ultrasonic transmission probe 11 with reference to the xz plane (see FIG. 4) and inspect the presence of an axial crack after inspecting the presence of a circumferential crack V2 on the pipe G. Thereby, not only the presence of a circumferential crack but also the presence of an axial crack can be inspected. The ultrasonic transmission probe 11 may be moved to be symmetrical to the ultrasonic reception probe 31 with reference to the xz plane instead of moving the ultrasonic reception probe 31.

The description has been made assuming that the piping inspection apparatus 100C includes one ultrasonic transmission probe 11 and two ultrasonic reception probes 21, 31 according to the fourth embodiment (see FIGS. 10 and 11), but the present invention is not limited thereto. For example, two ultrasonic transmission probes and one ultrasonic reception probe may be provided. With such a configuration, one ultrasonic transmission probe 11 is arranged to be symmetrical to the ultrasonic reception probe 21 with reference to the xz plane including the inspection site Q and perpendicular to the center axis (the y-axis) of the pipe G. Further, the other ultrasonic transmission probe (not illustrated) is arranged to be symmetrical to the ultrasonic reception probe 21 with reference to the yz plane including the inspection site Q and the center axis (the y-axis) of the pipe G.

Another ultrasonic transmission probe (not illustrated) arranged to be symmetrical to the ultrasonic reception probe 21 with reference to the yz plane may be added to the configuration of the fourth embodiment. That is, two ultrasonic transmission probes and two ultrasonic reception probes may be provided. Thereby, the presence of circumferential cracks at two points on the pipe G in the center axis direction (in the y-axis direction) can be inspected, thereby alleviating the working loads of the ultrasonic testing.

The description has been made assuming that the presence of damage at the circumferential welded part Gc is inspected according to each embodiment, but the base pipes Ga and Gb (see FIG. 1) can be inspected in a similar manner.

The description has been made assuming that the presence of damage on the pipe G is inspected in the water-wall W (see FIG. 1) for partitioning the inside and the outside of the boiler furnace (not illustrated) according to each embodiment, but the present invention is not limited thereto. That is, each embodiment can be applied to inspect various pipes provided in power plant or chemical plant. Many pipes (not illustrated) are provided near the walls in order to secure the installation space for devices (not illustrated) in power plant or the like in many cases. In this way, it is possible to appropriately inspect the presence of damage on a pipe in the method according to each embodiment even when a gap between the pipes and the wall is very small.

The description has been made assuming that the ultrasonic transmission probe 11 or the ultrasonic reception probe 21 employs an ultrasonic array probe according to each embodiment, but the present invention is not limited thereto. For example, other kind of probe such as single element type ultrasonic probe may be employed.

Each embodiment may be combined as needed. For example, the third embodiment and the fourth embodiment may be combined thereby to inspect the presence of an axial crack or circumferential crack on the pipe G and to specify a position of an axial crack (angle s: see FIGS. 8 and 9).

Each embodiment has been described in detail in order to understandably explain the present invention, and does not necessarily need to include all the components described above. Part of the configuration of each embodiment may be added with other configuration, deleted, or replaced therewith. Further, the aforementioned mechanisms or components, which are regarded necessary for the description, have been illustrated, and all the mechanisms and components for the products are not necessarily illustrated.

REFERENCE SIGNS LIST 100, 100A, 100B, 100C, 100D, 100E piping inspection apparatus
11, 11D ultrasonic transmission probe
11d wedge part
12 wedge (transmission wedge)
21 ultrasonic reception probe (first ultrasonic reception probe)
22 wedge (reception wedge, first reception wedge)
31 ultrasonic reception probe (second ultrasonic reception probe)
32 wedge (second reception wedge)
41 holding unit (first holding unit)
42 holding unit (second holding unit)
50 ultrasonic flaw detector
61 flaw detector control device (piping inspection unit)
G pipe
Gi thick part
Q inspection site

What is claimed is:
1. A piping inspection apparatus comprising:
an ultrasonic transmission probe arranged on a pipe and directed for transmitting an ultrasonic wave toward the pipe;
an ultrasonic reception probe arranged on the pipe and configured to receive an ultrasonic wave; and
a piping inspection unit for inspecting the presence of damage on the pipe on the basis of a reception result of the ultrasonic reception probe,
wherein the ultrasonic transmission probe is arranged such that an ultrasonic wave transmitted from the ultrasonic transmission probe toward the pipe propagates in a thick part of the pipe, is reflected on the outer peripheral face of the pipe once, and travels toward an inspection site on the pipe, and
the ultrasonic reception probe is arranged to be symmetrical to the ultrasonic transmission probe with reference to a plane including the inspection site and perpendicular to the center axis of the pipe.
2. A piping inspection apparatus comprising:
an ultrasonic transmission probe arranged on a pipe and directed for transmitting an ultrasonic wave toward the pipe;
an ultrasonic reception probe arranged on the pipe and configured to receive an ultrasonic wave; and
a piping inspection unit for inspecting the presence of damage on the pipe on the basis of a reception result of the ultrasonic reception probe,
wherein the ultrasonic transmission probe is arranged such that an ultrasonic wave transmitted from the ultrasonic transmission probe toward the pipe propagates in a thick part of the pipe, and is reflected on the outer peripheral face of the pipe once, and travels toward an inspection site on the pipe, and
the ultrasonic reception probe is arranged to be symmetrical to the ultrasonic transmission probe with reference to a plane including the inspection site and the center axis of the pipe.
3. The piping inspection apparatus according to claim 1, comprising:
a transmission wedge present between the ultrasonic transmission probe and the pipe;

a reception wedge present between the ultrasonic reception probe and the pipe; and a holding unit for holding a distance between the transmission wedge and the reception wedge.

4. The piping inspection apparatus according to claim 3, wherein the holding unit can is configured to adjust the distance.

5. The piping inspection apparatus according to claim 3, wherein the transmission wedge is arranged at an angle between 90° and 135° on the pipe in the circumferential direction with reference to a plane including the inspection site and the center axis of the pipe.

6. The piping inspection apparatus according to claim 1, wherein the piping inspection unit is configured to specify a circumferential position of the damage on the pipe on the basis of a ratio of a time after the ultrasonic transmission probe transmits an ultrasonic wave until the ultrasonic reception probe receives the ultrasonic wave while the ultrasonic transmission probe and the ultrasonic reception probe are arranged on one side in a plane including the inspection site and the center axis of the pipe to a time after the ultrasonic transmission probe transmits an ultrasonic wave until the ultrasonic reception probe receives the ultrasonic wave while the ultrasonic transmission probe and the ultrasonic reception probe are arranged on the other side in the plane including the inspection site and the center axis of the pipe.

7. The piping inspection apparatus according to claim 1, wherein the ultrasonic transmission probe and the ultrasonic reception probe are an ultrasonic array probe.

8. A piping inspection apparatus comprising:

an ultrasonic transmission probe arranged on a pipe and directed for transmitting an ultrasonic wave toward the pipe;

a first ultrasonic reception probe arranged on the pipe and configured to receive an ultrasonic wave;

a second ultrasonic reception probe arranged on the pipe and configured to receive an ultrasonic wave; and a piping inspection unit for inspecting the presence of damage on the pipe on the basis of a reception result of the first ultrasonic reception probe and a reception result of the second ultrasonic reception probe, wherein the ultrasonic transmission probe is arranged such that an ultrasonic wave transmitted from the ultrasonic transmission probe toward the pipe propagates in a thick part of the pipe, and is reflected on the outer peripheral face of the pipe once, and travels toward an inspection site on the pipe, the first ultrasonic reception probe is arranged to be symmetrical to the ultrasonic transmission probe with reference to a plane including the inspection site and perpendicular to the center axis of the pipe, and the second ultrasonic reception probe is arranged to be symmetrical to the ultrasonic transmission probe with reference to a plane including the inspection site and the center axis of the pipe.

9. The piping inspection apparatus according to claim 8, comprising:

a transmission wedge present between the ultrasonic transmission probe and the pipe;

a first reception wedge present between the first ultrasonic reception probe and the pipe;

a second reception wedge present between the second ultrasonic reception probe and the pipe;

a first holding unit for holding a distance between the transmission wedge and the first reception wedge; and a second holding unit for holding a distance between the transmission wedge and the second reception wedge.

10. The piping inspection apparatus according to claim 9, wherein the first holding unit is configured to adjust the distance between the transmission wedge and the first reception wedge, and the second holding unit is configured to adjust the distance between the transmission wedge and the second reception wedge.

* * * * *